(12) United States Patent
Amikura et al.

(10) Patent No.: US 10,424,466 B2
(45) Date of Patent: Sep. 24, 2019

(54) METHOD FOR INSPECTING SHOWER PLATE OF PLASMA PROCESSING APPARATUS

(71) Applicant: TOKYO ELECTRON LIMITED, Tokyo (JP)

(72) Inventors: Norihiko Amikura, Miyagi (JP); Risako Miyoshi, Miyagi (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 183 days.

(21) Appl. No.: 15/680,621

(22) Filed: Aug. 18, 2017

(65) Prior Publication Data

US 2018/0053637 A1    Feb. 22, 2018

(30) Foreign Application Priority Data

Aug. 19, 2016    (JP) .................... 2016-161147

(51) Int. Cl.
| | |
|---|---|
| *G01N 11/08* | (2006.01) |
| *G01N 19/08* | (2006.01) |
| *H01J 37/32* | (2006.01) |
| *G01L 19/00* | (2006.01) |

(52) U.S. Cl.
CPC .... *H01J 37/32798* (2013.01); *G01L 19/0007* (2013.01); *G01N 19/08* (2013.01); *H01J 37/32449* (2013.01); *H01J 2237/02* (2013.01)

(58) Field of Classification Search
CPC .... G01L 19/0007; G01N 11/00; G01N 11/08; G01N 19/08; H01J 37/32; H01J 37/32449; H01J 37/32798; H01J 2237/02
See application file for complete search history.

(56) References Cited

U.S. PATENT DOCUMENTS

| | | | | |
|---|---|---|---|---|
| 2006/0057301 A1* | 3/2006 | Konig | ............... | H05H 1/42 |
| | | | | 427/446 |
| 2013/0025715 A1* | 1/2013 | Yamaguchi | ............... | F17D 1/00 |
| | | | | 137/561 R |
| 2014/0332100 A1* | 11/2014 | Hayasaka | ............. | C23C 16/455 |
| | | | | 137/551 |

FOREIGN PATENT DOCUMENTS

| | | | | |
|---|---|---|---|---|
| CN | 1809794 A | 7/2006 | | |
| CN | 103928284 A | 7/2014 | | |
| JP | 2010287757 A | * 12/2010 | ......... | H01L 21/3065 |
| JP | 2013-51315 A | 3/2013 | | |

* cited by examiner

*Primary Examiner* — Nguyen Q. Ha
(74) *Attorney, Agent, or Firm* — Rothwell, Figg, Ernst & Manbeck, P.C.

(57) ABSTRACT

The present disclosure provides a method for inspecting a shower plate of a plasma processing apparatus. In the plasma processing apparatus, a gas ejection unit includes a shower plate. A plurality of gas ejection holes are formed on the shower plate. This method includes (i) setting a flow rate of gas output from a first flow rate controller, and (ii) acquiring a measurement value indicating a pressure in a flow path inside a second pressure control type flow rate controller by using a pressure gauge of the second flow rate controller in a state where the gas output from the first flow rate controller at the set flow rate is supplied to the gas ejection unit and branched between the first flow rate controller and the gas ejection unit so as to be supplied to the flow path inside the second flow rate controller.

8 Claims, 6 Drawing Sheets

METHOD FOR INSPECTING SHOWER PLATE OF PLASMA PROCESSING APPARATUS

CROSS-REFERENCE TO RELATED APPLICATIONS

This application is based on and claims priority from Japanese Patent Application No. 2016-161147, filed on Aug. 19, 2016, with the Japan Patent Office, the disclosure of which is incorporated herein in its entirety by reference.

TECHNICAL FIELD

An exemplary embodiment of the present disclosure relates to a method for inspecting a shower plate of a plasma processing apparatus.

BACKGROUND

A plasma processing apparatus is used in manufacturing an electronic device such as, for example, a semiconductor device. A capacitively coupled plasma processing apparatus is known as a type of the plasma processing apparatus. The capacitively coupled plasma processing apparatus includes a chamber body, a placing table, and a gas ejection unit.

The chamber body provides its internal space as a chamber. The placing table is provided inside the chamber and includes a lower electrode. The gas ejection unit includes a shower plate. The shower plate is provided above the placing table. A plurality of gas ejection holes are formed on the shower plate. The shower plate and/or the gas ejection unit constitute an upper electrode. Japanese Patent Laid-Open Publication No. 2013-051315 discloses this plasma processing apparatus.

SUMMARY

One aspect provides a method for inspecting a shower plate of a plasma processing apparatus. The plasma processing apparatus includes a chamber body, a placing table, and a gas ejection unit. The chamber body provides a chamber. The placing table is provided inside the chamber. The gas ejection unit includes a shower plate. The shower plate is provided above the placing table. A plurality of gas ejection holes are formed on the shower plate. The present method includes (i) setting a flow rate of gas output from a first flow rate controller, and (ii) acquiring a measurement value indicating a pressure in a flow path inside a second pressure control type flow rate controller by using a pressure gauge of the second flow rate controller in a state where the gas output from the first flow rate controller at the set flow rate is supplied to the gas ejection unit and branched between the first flow rate controller and the gas ejection unit so as to be supplied to the flow path inside the second flow rate controller.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which form a part hereof. The illustrative embodiments described in the detailed description, drawing, and claims are not meant to be limiting. Other embodiments may be utilized, and other changes may be made without departing from the spirit or scope of the subject matter presented here.

Diameters of the plurality of gas ejection holes of the shower plate vary with elapse of time for the plasma processing. Further, the diameters of the plurality of gas ejection holes may be different from a designed value due to a manufacture error. When the diameters of the plurality of gas ejection holes vary or are different from the designed value, the result of the plasma processing becomes different from a desired result. Thus, it is necessary to inspect the shower plate.

One aspect provides a method for inspecting a shower plate of a plasma processing apparatus. The plasma processing apparatus includes a chamber body, a placing table, and a gas ejection unit. The chamber body provides a chamber. The placing table is provided inside the chamber. The gas ejection unit includes a shower plate. The shower plate is provided above the placing table. A plurality of gas ejection holes are formed on the shower plate. The present method includes (i) setting a flow rate of gas output from a first flow rate controller, and (ii) acquiring a measurement value indicating a pressure in a flow path inside a pressure control type second flow rate controller by using a pressure gauge of the second flow rate controller in a state where the gas output from the first flow rate controller at the set flow rate is supplied to the gas ejection unit and branched between the first flow rate controller and the gas ejection unit so as to be supplied to the flow path inside the second pressure control type flow rate controller.

The pressure of the upstream side (the first flow rate controller side) of the gas ejection unit increases when the diameters of the gas ejection holes of the shower plate are small, and decreases when the diameters are large. That is, the pressure of the upstream side of the gas ejection unit reflects the size of the diameters of the gas ejection holes of the shower plate. In the above-described method, the gas output from the first flow rate controller is also supplied to the flow path inside the second flow rate controller, in addition to the gas ejection unit. Since the second flow rate controller is a pressure control type flow rate controller, it has a pressure gauge. The measurement value obtained by the pressure gauge indicates the pressure in the flow path inside the second flow rate controller, and reflects the pressure of the upstream side of the gas ejection unit. According to the present method, a measurement value reflecting the size of the diameters of the gas ejection holes of the shower plate may be obtained. Therefore, according to the present method, the shower plate may be inspected.

In one exemplary embodiment, the measurement value may be an average value of a plurality of instantaneous values of the pressure. In this exemplary embodiment, since an average value of a plurality of instantaneous values measured by the pressure gauge is obtained as the measurement value, an error caused by measurement accuracy of the pressure gauge of the second flow rate controller may be suppressed.

In one exemplary embodiment, a flow path length from the second flow rate controller to an opening end of the shower plate on the chamber side is equal to or less than 1.5 m. In this exemplary embodiment, the pressure measured by the pressure gauge largely varies depending on a change of the diameters of the gas ejection holes. Thus, the change of the diameters of the gas ejection holes may be detected with high sensitivity.

In one exemplary embodiment, the plurality of gas ejection holes constitute a plurality of gas ejection hole groups. In addition, the plasma processing apparatus further includes a flow splitter. The flow splitter has an input and a plurality of outputs. The input of the flow splitter is connected to the first flow rate controller. The plurality of outputs of the flow splitter are connected to the plurality of gas ejection hole groups, respectively.

In one exemplary embodiment, a pipe extending from the second flow rate controller is connected to a pipe connecting one of the plurality of outputs and one gas ejection hole group of the plurality of gas ejection hole groups to each other. In another exemplary embodiment, the pipe extending from the second flow rate controller may be connected to a pipe connecting the input of the flow splitter and the first flow rate controller to each other.

In another exemplary embodiment, the plurality of gas ejection hole groups are formed on a plurality of areas of the shower plate that are coaxial with an axis of the shower plate extending in a plate thickness, respectively. In addition, the plasma processing apparatus further includes: a plurality of first pipes; a plurality of pressure control type flow rate controllers, and a plurality of second pipes. The plurality of first pipes connect the plurality of outputs of the flow splitter and the plurality of gas ejection hole groups to each other, respectively. The plurality of second pipes connect the plurality of flow rate controllers and the plurality of first pipes to each other, respectively. In this exemplary embodiment, in the acquiring the measurement value, a measurement value indicating a pressure in a flow path inside one flow rate controller of the plurality of flow rate controllers that is connected to the one first pipe, as the second flow rate controller, is acquired using a pressure gauge of the one flow rate controller in a state where the gas output from the first flow rate controller at the set flow rate is supplied to the gas ejection unit through one first pipe of the plurality of first pipes that is connected to one gas ejection hole group selected from the plurality of gas ejection hole groups, and supplied to the flow path inside the one flow rate controller. The acquiring the measurement value is executed in the manner that each of the plurality of gas ejection hole groups is sequentially selected as the one gas ejection hole group. According to this exemplary embodiment, a measurement value of a pressure that reflects the diameters of the gas ejection holes of each of the plurality of gas ejection hole groups is acquired. Therefore, several measurement values reflecting distribution of the diameters of the gas ejection holes in the radial direction of the shower plate may be obtained.

In one exemplary embodiment, the method may further include comparing the measurement value with a reference value that is prepared in advance.

In one exemplary embodiment, a sequence including the setting the flow rate and the acquiring the measurement value is repeated using different flow rates, each as the flow rate, and a plurality of measurement values including the measurement value may be acquired.

As described above, since a measurement value reflecting the diameters of the gas ejection holes of the shower plate may be obtained, the shower plate may be inspected.

Hereinafter, various exemplary embodiments will be described in detail with reference to the drawings. Meanwhile, in the respective drawings, similar or corresponding parts will be denoted by their common reference numerals.

Figure 1:
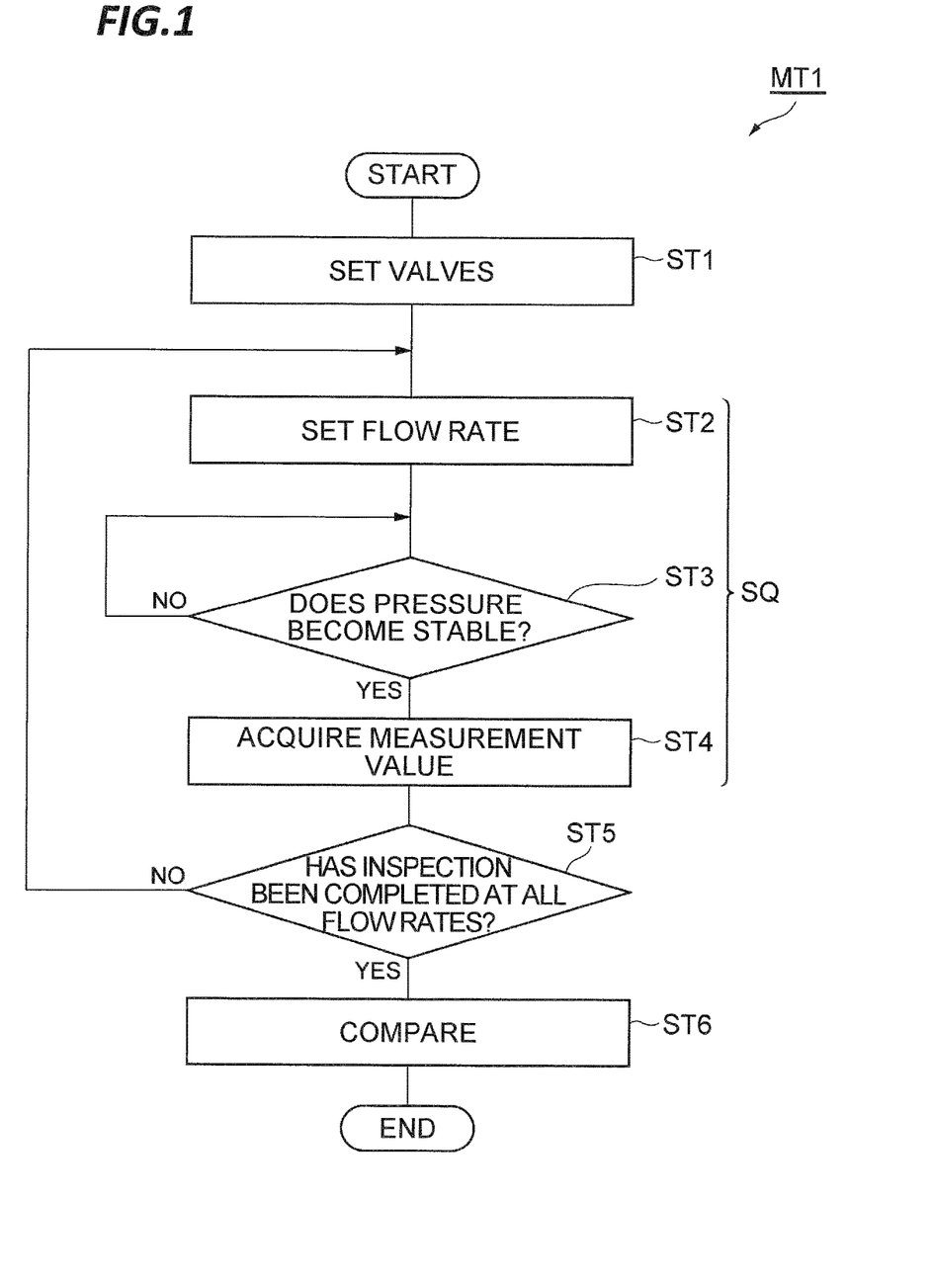
FIG. 1 is a flow chart illustrating a method for inspecting a shower plate of a plasma processing apparatus according to an exemplary embodiment.

FIG. 1 is a flow chart illustrating a method for inspecting a shower plate of a plasma processing apparatus according to an exemplary embodiment. In the method MT1 illustrated in FIG. 1, a measurement value reflecting the diameters of the plurality of gas ejection holes of the shower plate that eject gas into the chamber in the plasma processing apparatus is obtained. Hereinafter, prior to describing the method MT1 in detail, an example of a plasma processing apparatus to which the method MT1 may be applied will be described.

Figure 2:
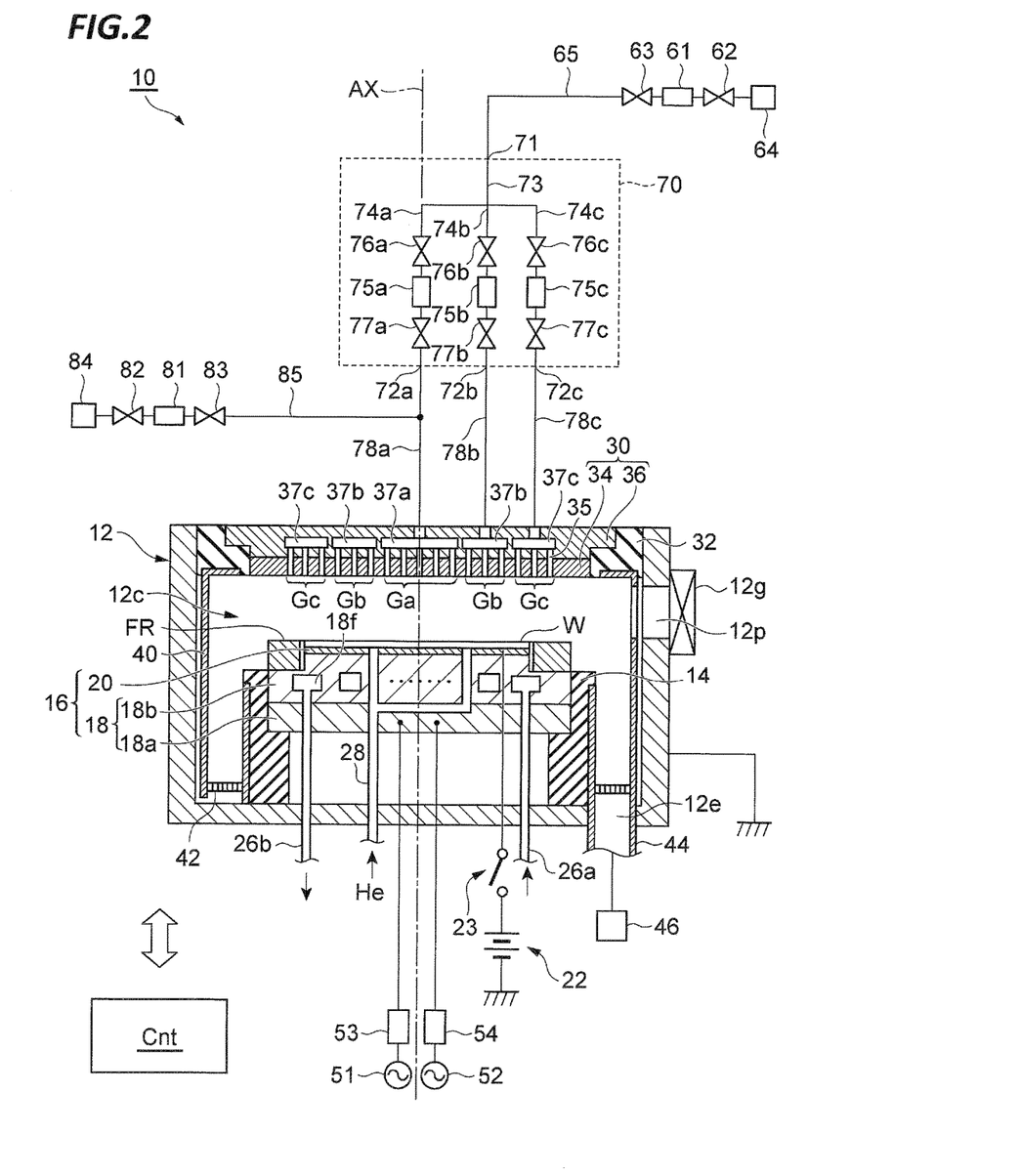
FIG. 2 is a view schematically illustrating a plasma processing apparatus to which the method illustrated in FIG. 1 may be applied.

FIG. 2 is a view schematically illustrating a plasma processing apparatus to which the method illustrated in FIG. 1 may be applied. A plasma processing apparatus 10 illustrated in FIG. 2 is a capacitively coupled plasma processing apparatus. The plasma processing apparatus 10 includes a chamber body 12. The chamber body 12 has a substantially cylindrical shape. The central axis of the chamber body 12 is substantially consistent with the vertically extending axis AX. The chamber body 12 provides its internal space as a chamber 12c. The chamber body 12 is formed of, for example, aluminum, and the inner wall surface thereof is anodized. The chamber body 12 is grounded. A carry-in/out port 12p for a workpiece W is formed on the side wall of the chamber body 12, and this carry-in/out port 12p is configured to be opened/closed by a gate valve 12g. Meanwhile, the workpiece W may have a substantially disc shape.

A support 14 is provided on the bottom portion of the chamber body 12. The support 14 is formed of, for example, an insulating material. The support 14 has a substantially cylindrical shape. The support 14 extends vertically from the bottom portion of the chamber body 12, inside the chamber 12c. A placing table 16 is provided inside the chamber 12c. The placing table 16 is supported by the support 14.

The placing table 16 holds the workpiece W on the top surface thereof. The placing table 16 has a lower electrode 18 and an electrostatic chuck 20. The lower electrode 18 includes a first plate 18a and a second plate 18b. The first plate 18a and the second plate 18b are formed of, for example, a metal (e.g., aluminum) and has a substantially disc shape. The second plate 18b is provided on the first plate 18a and electrically connected to the first plate 18a.

The electrostatic chuck 20 is provided on the second plate 18b. The electrostatic chuck 20 has an insulating layer and an electrode as a conductive film mounted in the insulating layer. A DC power supply 22 is electrically connected to the electrode of the electrostatic chuck 20 via a switch 23. This electrostatic chuck 20 adsorbs the workpiece W by an electrostatic force generated by a DC voltage from the DC power supply 22. As a result, the electrostatic chuck 20 may hold the workpiece W.

A focus ring FR is provided on the circumferential edge of the second plate 18b to surround the edge of the workpiece W and the electrostatic chuck 20. The focus ring FR is provided to improve the uniformity of the plasma processing. The focus ring FR may be formed of a material such as, for example, silicon, quartz, or SiC.

A flow path 18f is formed inside the second plate 18b. A refrigerant is supplied to the flow path 18f from a chiller unit provided outside the chamber body 12 through a pipe 26a. The refrigerant supplied to the flow path 18f is returned to the chiller unit through a pipe 26b. In this way, the refrigerant is supplied to be circulated in the flow path 18f. By controlling the temperature of the refrigerant, the temperature of the workpiece W held by the electrostatic chuck 20 is controlled.

A gas supply line 28 is formed in the plasma processing apparatus 10. The gas supply line 28 supplies heat transfer gas, for example, He gas from a heat transfer gas supply mechanism to the space between the top surface of the electrostatic chuck 20 and the rear surface of the workpiece W.

The plasma processing apparatus 10 further includes a gas ejection unit 30. The gas ejection unit 30 is configured to eject gas into the chamber 12c. The gas ejection unit 30 constitutes an upper electrode. The gas ejection unit 30 is provided above the placing table 16 via the space inside the chamber 12c. The gas ejection unit 30 is supported on the top portion of the chamber body 12 via a member 32. The member 32 may have an insulating property.

The gas ejection unit 30 has a shower plate 34 and a support body 36. The shower plate 34 is provided above the placing table 16. The shower plate 34 faces the chamber 12c. The shower plate 34 may be formed of, for example, silicon or silicon oxide. Alternatively, the shower plate 34 may be formed by performing a ceramic coating on a conductive base material (e.g., aluminum).

A plurality of gas ejection holes 35 are formed on the shower plate 34. The plurality of gas ejection holes 35 penetrate the shower plate 34 in the plate thickness direction of the shower plate 34. In one exemplary embodiment, the plurality of gas ejection holes 35 constitute a plurality of gas ejection hole groups Ga, Gb, and Gc. That is, among the plurality of gas ejection holes 35, some gas ejection holes constitute the gas ejection hole group Ga, other some gas ejection holes 35 constitute the gas ejection hole group Gb, and the other some gas ejection holes constitute the gas ejection hole group Gc. Meanwhile, the number of the gas ejection hole groups may be arbitrary.

The gas ejection holes 35 of the gas ejection hole group Ga, the gas ejection holes 35 of the gas ejection hole group Gb, and the gas ejection holes 35 of the gas ejection hole group Gc are formed on a plurality of areas of the shower plate 34 that are coaxial with the axis AX. Specifically, the gas ejection holes 35 of the gas ejection hole group Ga are formed on the area crossing the axis AX. The gas ejection holes 35 of the gas ejection hole group Gb are formed on the area outside the area where the gas ejection holes 35 of the gas ejection hole group Ga are formed. The gas ejection holes 35 of the gas ejection hole group Gc are formed on the area outside the area where the gas ejection holes 35 of the gas ejection hole group Gb are formed.

The support body 36 is configured to detachably support the shower plate 34. The support body 36 may be formed of a conductive material such as, for example, aluminum. A plurality of gas diffusion chambers 37a, 37b, and 37c are formed inside the support body 36. The plurality of gas diffusion chambers 37a, 37b, and 37c are formed to be coaxial with the axis AX and separated from each other. The gas diffusion chamber 37a is formed in the area crossing the axis AX. The gas diffusion chamber 37b is formed to extend circumferentially around the axis AX outside the gas diffusion chamber 37a. The gas diffusion chamber 37c is formed to extend circumferentially around the axis AX outside the gas diffusion chamber 37b. Meanwhile, the number of the gas diffusion chambers may be the same as the number of the gas ejection hole groups.

In the support body 36, a plurality of holes are formed to extend downward from the gas diffusion chambers 37a, 37b, and 37c and communicate with the plurality of gas ejection holes 35, respectively. Accordingly, the gas ejection holes 35 of the gas ejection hole group Ga are connected to the gas diffusion chamber 37a, the gas ejection holes 35 of the gas ejection hole group Gb are connected to the gas diffusion chamber 37b, and the gas ejection holes 35 of the gas ejection hole group Gc are connected to the gas diffusion chamber 37c.

In the plasma processing apparatus 10, a shield 40 is detachably provided along the inner wall of the chamber body 12. The shield 40 is also provided on the outer periphery of the support 14. The shield 40 suppresses byproducts of the plasma processing from being attached to the chamber body 12. The shield 40 may be formed by coating a base material made of, for example, aluminum with ceramic (e.g., $Y_2O_3$).

A baffle plate 42 is provided on the bottom portion side of the chamber body 12 and between the support 14 and the side wall of the chamber body 12. The baffle plate 42 may be formed by coating a base material made of, for example, aluminum with ceramic (e.g., $Y_2O_3$). A large number of through holes are formed on the baffle plate 42. An exhaust port 12e is formed below the baffle plate 42 in the chamber body 12. An exhaust device 46 is connected to the exhaust port 12e via an exhaust pipe 44. The exhaust device 46 may have a pressure regulating valve. Further, the exhaust device 46 may have a turbo molecular pump and/or a dry pump.

The plasma processing apparatus 10 further includes a first high frequency power supply 51 and a second high frequency power supply 52. The first high frequency power supply 51 generates a first high frequency wave for plasma generation. The frequency of the first high frequency wave is within a range of, for example, 27 MHz to 100 MHz. The first high frequency power supply 51 is connected to the lower electrode 18 via a matching unit 53. The matching unit 53 has a circuit for matching the output impedance of the first high frequency power supply 51 and the impedance of a load side (the lower electrode 18 side) with each other. Meanwhile, the first high frequency power supply 51 may be connected to the upper electrode via the matching unit 53.

The second high frequency power supply 52 generates a second high frequency wave for attracting ions into the workpiece W, that is, a high frequency wave for bias. The frequency of the second high frequency wave is within a range of, for example, 400 kHz to 13.56 MHz. The second high frequency power supply 52 is connected to the lower electrode 18 via a matching unit 54. The matching unit 54 has a circuit for matching the output impedance of the second high frequency power supply 52 and the impedance of a load side (the lower electrode 18 side) with each other.

In addition, the plasma processing apparatus 10 further includes a first flow rate controller 61. The first flow rate controller 61 is a device that controls the flow rate of the gas supplied to the gas ejection unit 30. The first flow rate controller 61 may be a pressure control type flow rate controller or a mass flow controller. The first flow rate controller 61 is connected to a gas source 64 via a valve 62. Further, the first flow rate controller 61 is connected to an input 71 of a flow splitter 70 via a valve 63 and a common pipe 65.

The flow splitter 70 has the input 71 and a plurality of outputs 72a, 72b, and 72c. The number of the outputs of the flow splitter 70 may be the same as the number of the gas ejection hole groups.

The flow splitter 70 is configured to distribute the gas supplied from the first flow rate controller 61 to the input 71, to each of the plurality of outputs 72a, 72b, and 72c. In the flow splitter 70, a common gas line 73 extends from the input 71. The common gas line 73 is branched into a plurality of gas lines 74a, 74b, and 74c. The plurality of gas lines 74a, 74b, and 74c extend to the plurality of outputs 72a, 72b, and 72c, respectively.

Each of the plurality of gas lines 74a, 74b, and 74c includes a flow rate controller and two valves. Specifically, the gas line 74a includes a flow rate controller 75a and valves 76a and 77a. The valve 76a is provided on the upstream side (the first flow rate controller 61 side) of the flow rate controller 75a. The valve 77a is provided on the downstream side of the flow rate controller 75a. The gas line 74b includes a flow rate controller 75b and valves 76b and 77b. The valve 76b is provided on the upstream side of the flow rate controller 75b. The valve 77b is provided on the downstream side of the flow rate controller 75b. Further, the gas line 74c includes a flow rate controller 75c and valves 76c and 77c. The valve 76c is provided on the upstream side of the flow rate controller 75c. The valve 77c is provided on the downstream side of the flow rate controller 75c. Each of the flow rate controllers 75a, 75b, and 75c of the flow splitter 70 may be a mass flow controller. That is, each of the flow rate controllers 75a, 75b, and 75c is configured to control the flow rate of gas to be output, by measuring the flow rate by a flow rate sensor (e.g., a thermal sensor) rather than the pressure gauge.

The plurality of outputs 72a, 72b, and 72c of the flow splitter 70 are connected to the plurality of gas ejection hole groups Ga, Gb, and Gc, respectively, via the plurality of first pipes. Specifically, the output 72a is connected to the gas diffusion chamber 37a via a first pipe 78a. As described above, the gas diffusion chamber 37a is connected to the gas ejection holes 35 of the gas ejection hole group Ga. The output 72b is connected to the gas diffusion chamber 37b via a first pipe 78b. As described above, the gas diffusion chamber 37b is connected to the gas ejection holes 35 of the gas ejection hole group Gb. Further, the output 72c is connected to the gas diffusion chamber 37c via a first pipe 78c. As described above, the gas diffusion chamber 37c is connected to the gas ejection holes 35 of the gas ejection hole group Gc.

In addition, the plasma processing apparatus 10 further includes a flow rate controller 81. The flow rate controller 81 is a device that controls the flow rate of gas and is used as the second flow rate controller in the method MT1. The gas output from the flow rate controller 81 is added to the gas output from the first flow rate controller 61 in the downstream of the first flow rate controller 61 and the upstream of the gas ejection unit 30. The flow rate controller 81 is connected to a gas source 84 via a valve 82 on the primary side (or the upstream side) of the flow rate controller 81. The flow rate controller 81 is connected to one first pipe of the plurality of first pipes 78a, 78b, and 78c via a valve 83 on the secondary side (or the downstream side) of the flow rate controller 81, and a second pipe 85. In the exemplary embodiment illustrated in FIG. 2, the flow rate controller 81 is connected to the first pipe 78a.

In one exemplary embodiment, the flow path length from the flow rate controller 81 to the opening end of the shower plate 34 on the chamber 12c side is equal to or less than 1.5 m. The flow path length may be defined as the shortest flow path length from the output end of the flow rate controller 81 to the opening end of the shower plate 34 (the opening ends of the plurality of gas ejection holes 35 on the chamber 12c side). Specifically, in the plasma processing apparatus 10, the flow path length is the shortest flow path length from the output end of the flow rate controller 81 to the opening ends of the plurality of gas ejection holes 35 of the gas ejection hole group Ga through the second pipe 85, the first pipe 78a, and the gas diffusion chamber 37a.

Figure 3:
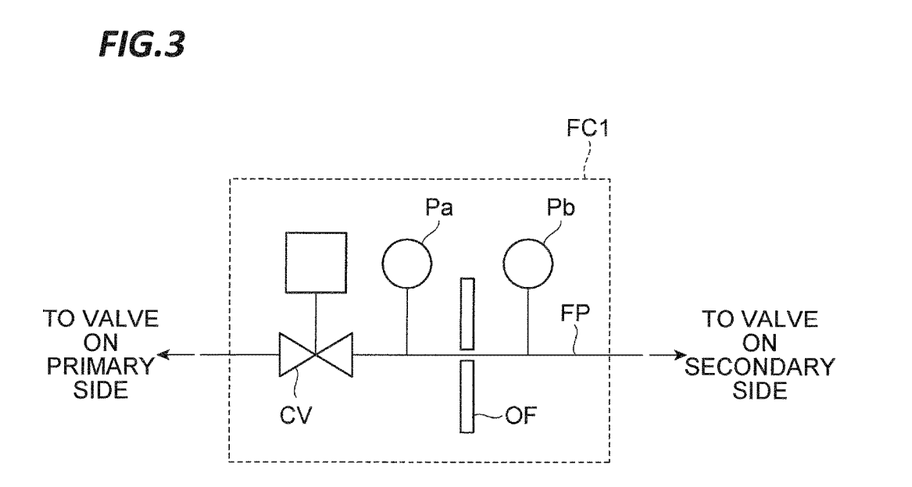
FIG. 3 is a view illustrating an example of a pressure control type flow rate controller.
Figure 4:
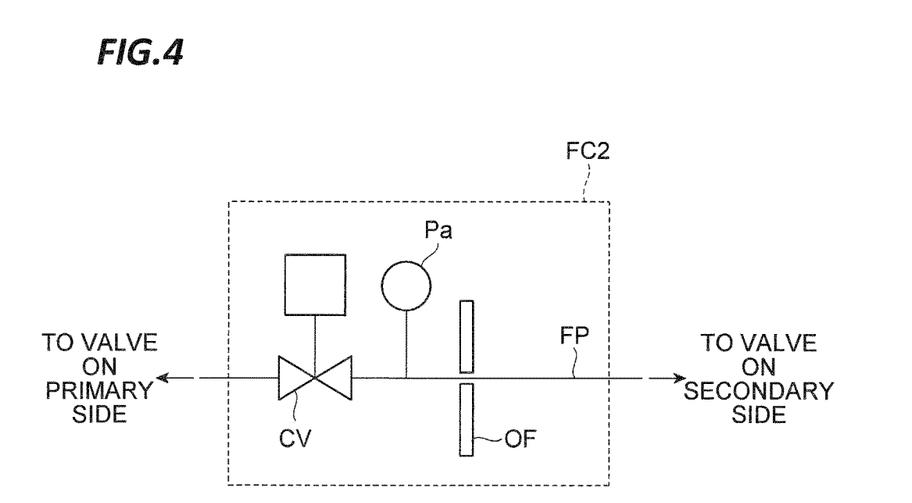
FIG. 4 is a view illustrating another example of the pressure control type flow rate controller.

The flow rate controller 81 is a pressure control type flow rate controller. As the flow rate controller 81, a flow rate controller FC1 illustrated in FIG. 3 or a flow rate controller FC2 illustrated in FIG. 4 is used. FIG. 3 is a view illustrating an example of the pressure control type flow rate controller. FIG. 4 is a view illustrating another example of the pressure control type flow rate controller.

The flow rate controller FC1 illustrated in FIG. 3 includes a control valve CV, an orifice member OF, and pressure gauges Pa and Pb. The control valve CV constitutes a part of a flow path FP inside the flow rate controller FC1. The control valve CV regulates its opening degree so as to regulate the flow rate of gas flowing in the downstream of the control valve CV. The orifice member OF provides an orifice on the downstream side of the control valve CV. The orifice reduces the cross-sectional area of the flow path FP. The pressure gauge Pa measures the pressure of the flow path FP between the orifice and the control valve CV. The pressure gauge Pb measures the pressure of the flow path FP on the downstream side of the orifice.

In the flow rate controller FC1, when the pressure of the flow path FP on the upstream side of the orifice is twice or more the pressure of the flow path FP on the downstream side of the orifice, the opening degree of the control valve CV is controlled so as to reduce a difference between the flow rate calculated from a value of the pressure measured by the pressure gauge Pa and a set flow rate. Further, in the flow rate controller FC1, when the pressure of the flow path FP on the upstream side of the orifice is smaller than twice the pressure of the flow path FP on the downstream side of the orifice, the opening degree of the control valve CV is controlled so as to reduce a difference between the flow rate calculated from a difference between a value of the pressure measured by the pressure gauge Pa and a value of the pressure measured by the pressure gauge Pb, and the set flow rate.

The flow rate controller FC2 illustrated in FIG. 4 is different from the flow rate controller FC1 in that the flow rate controller FC2 does not have the pressure gauge Pb. The flow rate controller FC2 is used on the premise that the pressure of the flow path FP on the upstream side of the orifice is twice or more the pressure of the flow path FP on the downstream side of the orifice. In the flow rate controller FC2, the opening degree of the control valve CV is controlled so as to reduce a difference between the flow rate calculated from a value of the pressure measured by the pressure gauge Pa and a set flow rate.

In one exemplary embodiment, the plasma processing apparatus 10 may further include a controller Cnt. The controller Cnt is a computer provided with, for example, a processor, a memory device, an input device, and a display device. The controller Cnt controls the respective units of the plasma processing apparatus 10 for the plasma processing executed by the plasma processing apparatus 10. Further, the controller Cnt controls the respective units of the plasma processing apparatus 10 in the method MT1, and may control calculations to be described later in the method MT1.

Hereinafter, the method MT1 will be described in detail by describing a case where the method MT1 is applied to the plasma processing apparatus 10, as an example. Meanwhile, in the method MT1, the pressure gauge of the flow rate controller 81 is used for the pressure measurement. Either the flow rate controller FC1 or the flow rate controller FC2 is used as the flow rate controller 81. When the flow rate controller FC1 is used as the flow rate controller 81, the pressure gauge used for the pressure measurement in the method MT1 may be any one of the pressure gauges Pa and Pb. When the flow rate controller FC2 is used as the flow rate controller 81, the pressure gauge used for the pressure measurement in the method MT1 is the pressure gauge Pa. In the following descriptions, the pressure gauge of the flow rate controller 81 that is used for the pressure measurement in the method MT1 will be referred to as a "pressure gauge P."

As illustrated in FIG. 1, a step ST1 is first executed in the method MT1. In the step ST1, setting of the various valves is executed. Specifically, the valve 62 on the primary side of the first flow rate controller 61 and the valve 63 on the secondary side thereof are opened. Further, among the gas lines 74a, 74b, and 74c of the flow splitter 70, two valves of a specific gas line connected to the first pipe to which the second pipe 85 is connected are opened. In the plasma processing apparatus 10, the two valves 76a and 77a of the gas line 74a are opened. Further, among the gas lines 74a, 74b, and 74c of the flow splitter 70, two valves of each of the gas lines other than the specific gas line are closed. In the plasma processing apparatus 10, the two valves 76b and 77b of the gas line 74b and the two valves 76c and 77c of the gas line 74c are closed. Further, the valve 82 on the primary side of the flow rate controller 81 is closed, and the valve 83 on the secondary side of the flow rate controller 81 is opened.

In a subsequent step ST2, the flow rate of the gas output from the first flow rate controller 61 is set to a designated flow rate. By the execution of the step ST2, the gas output from the first flow rate controller 61 at the set flow rate is supplied to the gas ejection unit 30 and branched between the first flow rate controller 61 and the gas ejection unit 30 so as to be supplied to the flow path FP inside the flow rate controller 81.

In a subsequent step ST3, it is determined whether a value of the pressure measured by the pressure gauge P of the flow rate controller 81 becomes stable. For example, it is determined whether a fluctuation amount of the value of the pressure measured by the pressure gauge P is equal to or less than a predetermined value. When it is determined in the step ST3 that the value of the pressure does not become stable, the step ST3 is executed again after elapse of predetermined time. Meanwhile, when it is determined in the step ST3 that the value of the pressure becomes stable, a step ST4 is executed.

In the step ST4, in a state where the gas output from the first flow rate controller 61 is supplied to the gas ejection unit 30 and the flow path FP inside the flow rate controller 81, a measurement value indicating the pressure in the flow path FP inside the flow rate controller 81 is acquired using the pressure gauge P of the flow rate controller 81. In one exemplary embodiment, the measurement value acquired in the step ST4 may be an average value of a plurality of instantaneous values of the pressure in the flow path FP of the flow rate controller 81. The plurality of instantaneous values are acquired for time length of, for example, 10 seconds.

In a subsequent step ST5, it is determined whether the inspection using all the plurality of different flow rates has been completed. Specifically, it is determined whether all the plurality of different flow rates have been designated in the first flow rate controller 61. When it is determined in the step ST5 that the inspection using all the flow rates has not been completed, the processing from the step ST2 is executed again. When the step ST2 is executed again, the flow rate of the gas output from the first flow rate controller 61 is set to another flow rate that has not been used for the inspection, among the plurality of different flow rates. When the sequence SQ including the steps ST2 and ST4 is repeated, a plurality of measurement values may be obtained.

Meanwhile, when it is determined in the step ST5 that the inspection using all the flow rates has been completed, a step ST6 is executed. In the step ST6, the plurality of measurement values are compared with a plurality of reference values, respectively. For example, when at least one of the plurality of measurement values is largely different from its corresponding reference value among the plurality of reference values, abnormality of the shower plate 34 is detected. More specifically, when an absolute value of a difference between at least one of the plurality of measurement values and its corresponding reference value is larger than a threshold value, abnormality of the shower plate 34 is detected. Alternatively, when the sum of absolute values of differences between the plurality of measurement values and the plurality of reference values, respectively, is larger than a threshold value, abnormality of the shower plate 34 is detected.

The plurality of reference values are numerical values prepared in advance. In a first example, the plurality of reference values are a plurality of measurement values acquired by executing the method MT1 when the shower plate 34 is initially introduced in the plasma processing apparatus 10. In a second example, the plurality of reference values are a plurality of measurement values acquired by applying the method MT1 to another plasma processing apparatus that has the same configuration as that of the plasma processing apparatus 10 and executes the same processing in parallel with the plasma processing apparatus 10. In a third example, the plurality of reference values are a plurality of measurement values acquired by applying the method MT1 to a reference plasma processing apparatus that has the same configuration as that of the plasma processing apparatus 10. Meanwhile, the reference plasma processing apparatus may have a shower plate on which a plurality of gas ejection holes each having a substantially similar diameter to the designed value are formed.

The pressure of the upstream side (the first flow rate controller 61 side) of the gas ejection unit 30 increases when the diameters of the gas ejection holes 35 of the shower plate 34 are small, and decreases when the diameters are large. That is, the pressure of the upstream side of the gas ejection unit 30 reflects the size of the diameters of the gas ejection holes 35 of the shower plate 34. In the method MT1, the gas output from the first flow rate controller 61 is also supplied to the flow path FP inside the flow rate controller 81, in addition to the gas ejection unit 30. Since the flow rate controller 81 is a pressure control type flow rate controller, it has the pressure gauge P. The measurement value obtained by the pressure gauge P indicates the pressure in the flow path FP inside the flow rate controller 81, and indicates the pressure of the upstream side of the gas ejection unit 30.

Thus, according to the method MT1, a measurement value reflecting the size of the diameters of the gas ejection holes 35 of the shower plate 34 may be obtained. Therefore, according to the method MT1, the shower plate 34 may be inspected.

As described above, in one exemplary embodiment, the measurement value is an average value of a plurality of instantaneous values of the pressure measured by the pressure gauge P. In this exemplary embodiment, an error caused by the measurement accuracy of the pressure gauge P of the flow rate controller 81 is suppressed.

Further, as described above, in one exemplary embodiment, the flow path length from the flow rate controller 81 to the open end of the shower plate 34 on the chamber 12c side is equal to or less than 1.5 m. In this exemplary embodiment, the pressure measured by the pressure gauge P largely varies depending on a change of the diameters of the gas ejection holes 35. Therefore, the change of the diameters of the gas ejection holes 35 may be detected with high sensitivity.

Further, the above-described reference values in the first example are measurement values acquired by executing the method MT1 when the shower plate 34 is initially introduced in the plasma processing apparatus 10. By comparing the reference values of the first example and the measurement values with each other, the occurrence/non-occurrence of deterioration of the shower plate 34 is detected.

Further, the above-described reference values in the second example are measurement values acquired by applying the method MT1 to another plasma processing apparatus that has the same configuration as that of the plasma processing apparatus 10 and executes the same processing in parallel with the plasma processing apparatus 10. By comparing the reference values of the second example and the measurement values with each other, the occurrence/non-occurrence of a machine difference related to the shower plate among the plurality of plasma processing apparatuses is detected.

Further, the above-described reference values in the third example are measurement values acquired by applying the method MT1 to a reference plasma processing apparatus that has the same configuration as that of the plasma processing apparatus 10. The reference plasma processing apparatus may have a shower plate on which a plurality of gas ejection holes each having a substantially similar diameter to the designed value are formed. By comparing the reference values of the third example and the measurement values with each other, the occurrence/non-occurrence of a difference between the diameters of the gas ejection holes 35 of the shower plate 34 in the plasma processing apparatus 10 and the designed value may be detected.

Hereinafter, descriptions will be made on results of first to eighth simulations for the flow path length L from the flow rate controller 81 to the opening end of the shower plate 34 on the chamber 12c side. In the first to eighth simulations, the inner diameter of each of the common pipe 65, the first pipes 78a, 78b, and 78c, and the second pipe 85 of the plasma processing apparatus 10 was set to 2.175 mm. In the first and fifth simulations, the flow path length L was set to 1 m. In the second and sixth simulations, the flow path length L was set to 1.5 m. In the third and seventh simulations, the flow path length L was set to 3 m. In the fourth and eighth simulations, the flow path length L was set to 4 m.

Then, in the first to eighth simulations, the opening/closing state of the various valves of the plasma processing apparatus 10 was set as described above with respect to the step ST1, and the pressure of the flow path FP inside the flow rate controller 81 was calculated from an actually measured value of the pressure of the gas diffusion chamber directly above the shower plate when gas was being output at a flow rate of 1,000 sccm from the first flow rate controller 61. Meanwhile, when the actually measured value of the pressure that was used in the first to fourth simulations was obtained, the diameter of each of the gas ejection holes of the shower plate was about 0.8 mm. Further, when the actually measured value of the pressure that was used in the fifth to eighth simulations was obtained, the diameter of each of the gas ejection holes of the shower plate was about 0.5 mm. In addition, an absolute value of a difference between the pressure of the first simulation and the pressure of the fifth simulation, an absolute value of a difference between the pressure of the second simulation and the pressure of the sixth simulation, an absolute value of a difference between the pressure of the third simulation and the pressure of the seventh simulation, and an absolute value of a difference between the pressure of the fourth simulation and the pressure of the eighth simulation were calculated.

As a result, the absolute value of the difference between the pressure of the first simulation and the pressure of the fifth simulation, the absolute value of the difference between the pressure of the second simulation and the pressure of the sixth simulation, the absolute value of the difference between the pressure of the third simulation and the pressure of the seventh simulation, and the absolute value of the difference between the pressure of the fourth simulation and the eighth simulation were 0.63 Torr, 0.52 Torr, 0.38 Torr, and 0.33 Torr, respectively. Since the measurement accuracy of the pressure gauge P of the flow rate controller 81 is ±0.2 Torr, when the flow path length L is a flow path length from which a difference larger than 0.4 Torr may be obtained as the absolute value of the difference of the pressures as described above, the difference between the diameters of the gas ejection holes that were set in the first to fourth simulations and the diameters of the gas ejection holes that were set in the fifth to eighth simulations may be detected. Accordingly, from the first to eighth simulations, it is confirmed that the flow path length L is required to be equal to or less than 1.5 m.

Figure 5:
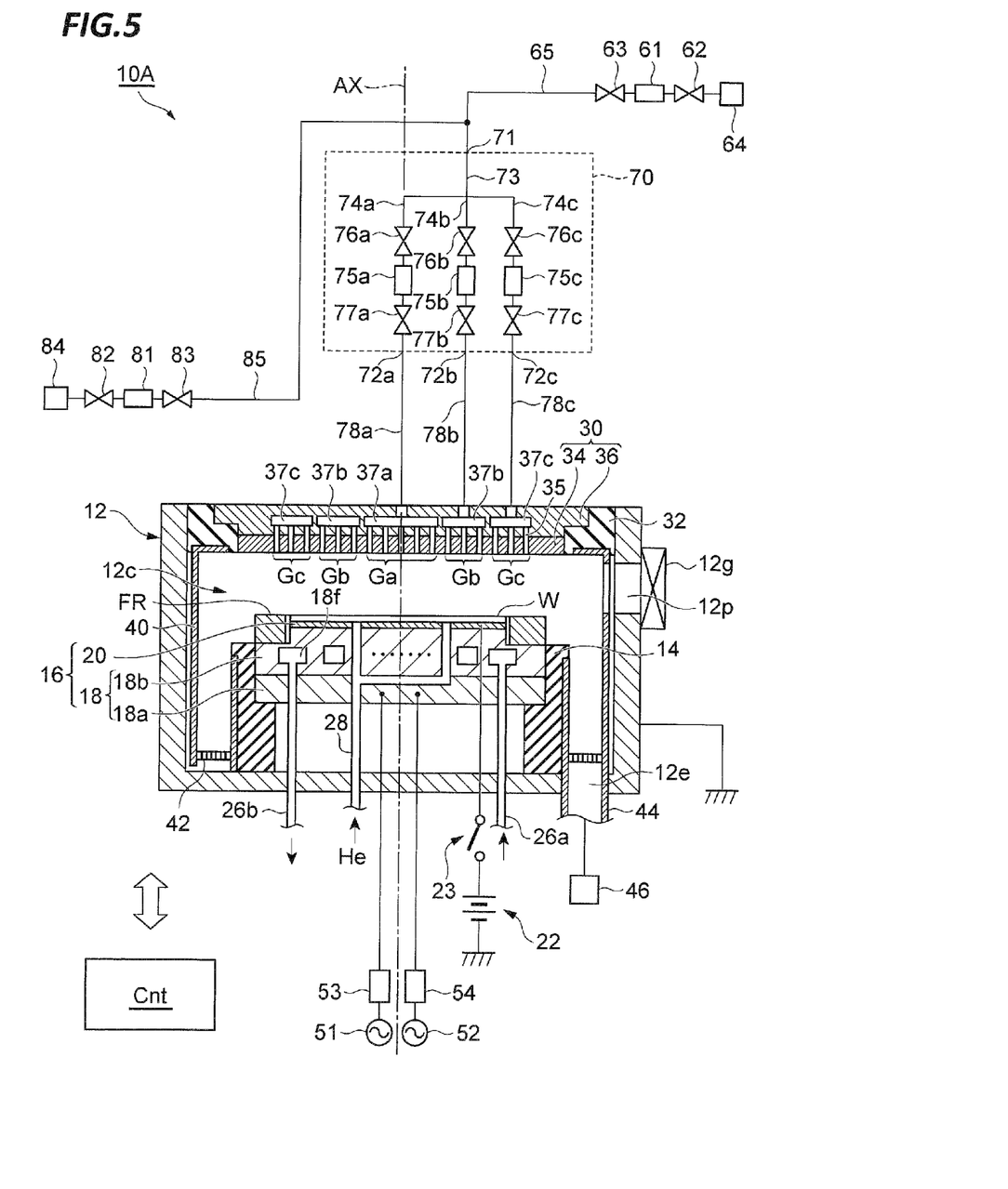
FIG. 5 is a view schematically illustrating another plasma processing apparatus to which the method illustrated in FIG. 1 may be applied.

Hereinafter, another plasma processing apparatus to which the method MT1 may be applied will be described. FIG. 5 is a view schematically illustrating another plasma processing apparatus to which the method illustrated in FIG. 1 may be applied. In the plasma processing apparatus 10, the second pipe 85 is connected to the first pipe 78a between the flow splitter 70 and the gas ejection unit 30. However, as illustrated in FIG. 5, the second pipe 85 may be connected to the pipe of the upstream side of the flow splitter 70. Specifically, as illustrated in FIG. 5, the second pipe 85 may be connected to the common pipe 65, rather than the first pipe 78a. In a plasma processing apparatus 10A illustrated in FIG. 5 as well, the flow path length from the flow rate controller 81 to the open end of the shower plate 34 on the chamber 12c side may be set to be equal to or less than 1.5 m.

Figure 6:
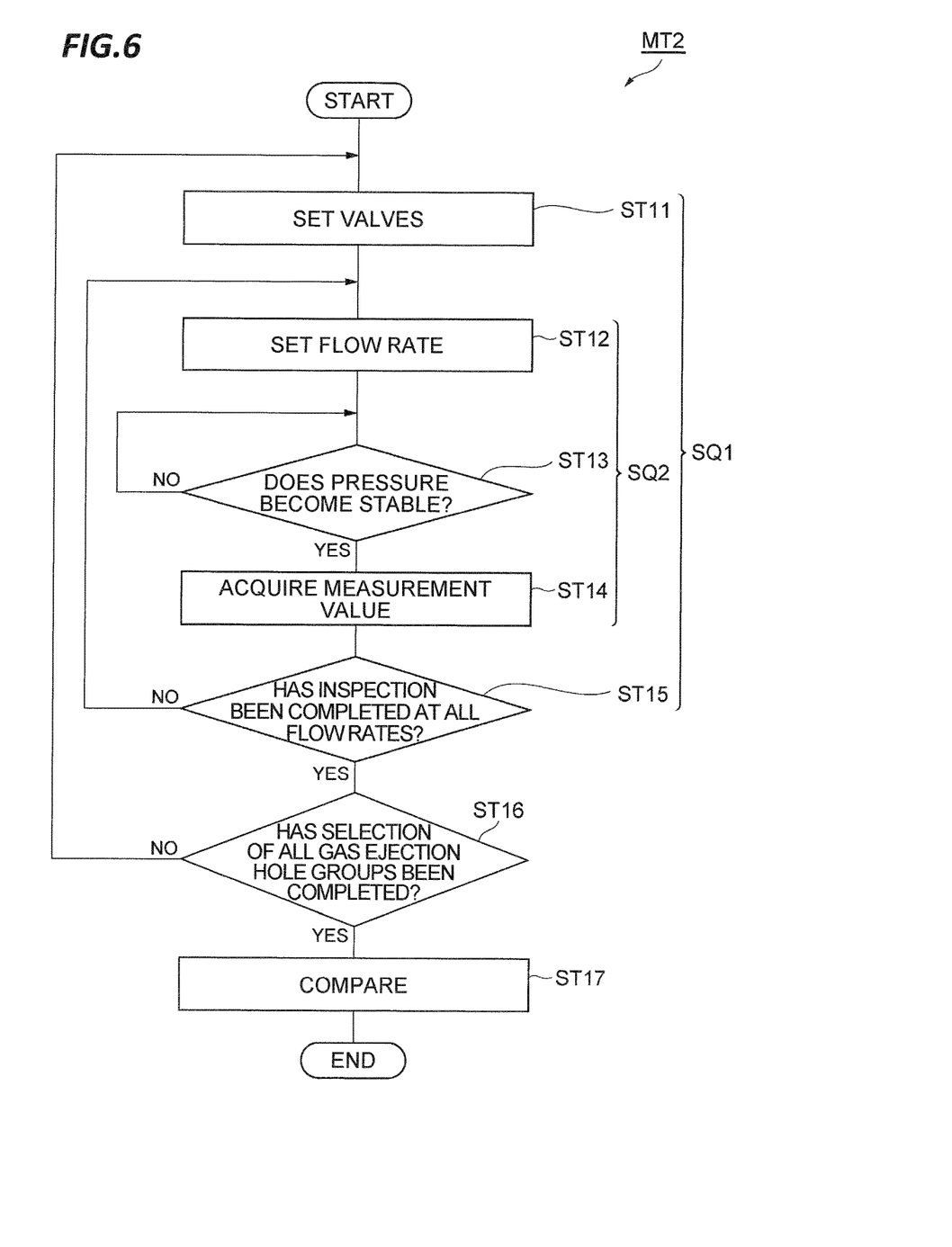
FIG. 6 is a flow chart illustrating a method for inspecting a shower plate of a plasma processing apparatus according to another exemplary embodiment.

Hereinafter, a method for inspecting the shower plate of the plasma processing apparatus according to another exemplary embodiment will be described. FIG. 6 is a flow chart illustrating a method for inspecting the shower plate of the plasma processing apparatus according to another exemplary embodiment. In a method MT2 illustrated in FIG. 6, the inspection of the shower plate is performed for each of the gas ejection hole groups. Hereinafter, prior to describing the method MT in detail, an example of a plasma processing apparatus to which the method MT2 may be applied will be described.

Figure 7:
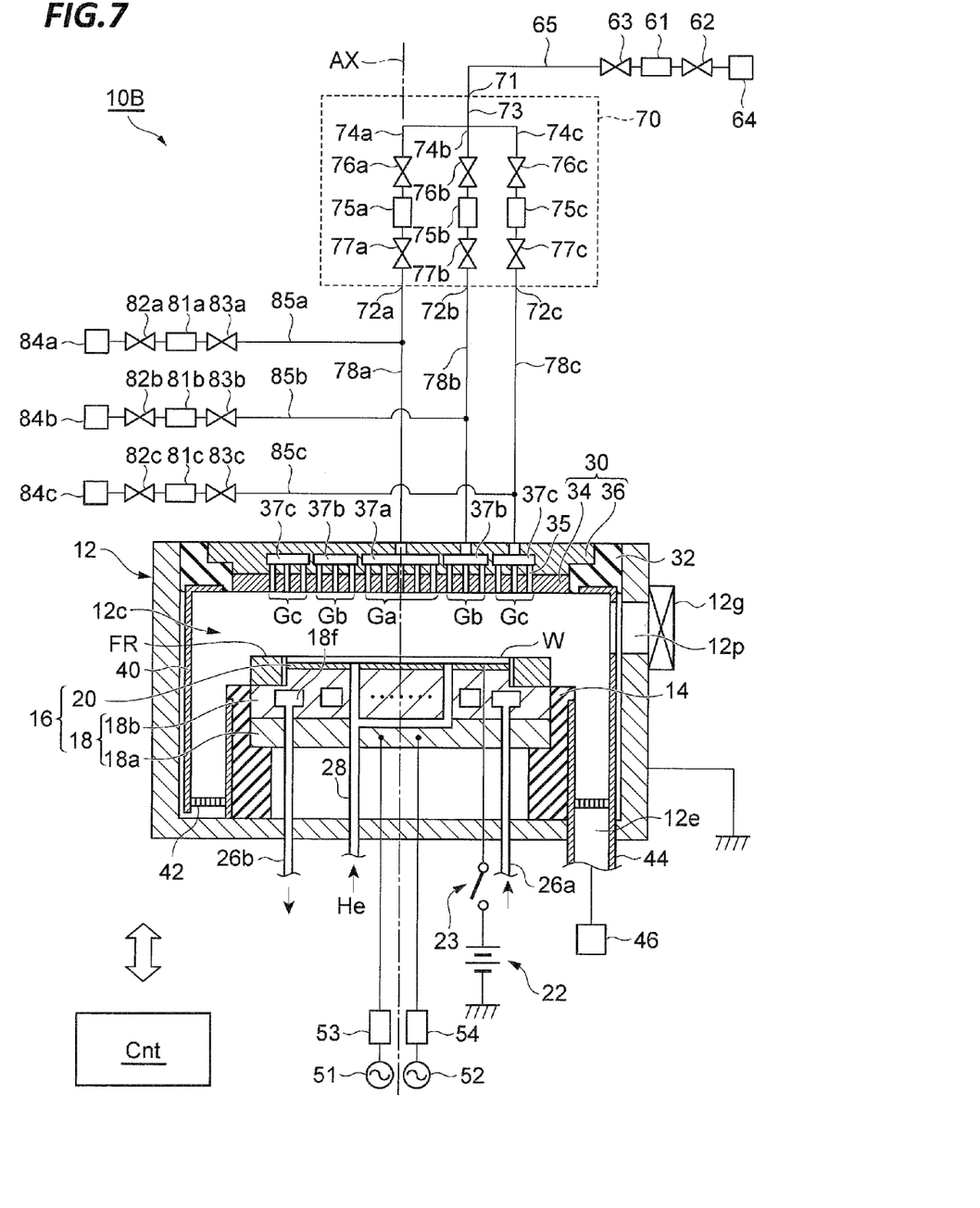
FIG. 7 is a view schematically illustrating a plasma processing apparatus to which the method illustrated in FIG. 6 may be applied.

FIG. 7 is a view schematically illustrating a plasma processing apparatus to which the method illustrated in FIG. 6 may be applied. A plasma processing apparatus 10B illustrated in FIG. 7 is different from the plasma processing apparatus 10 in that the plasma processing apparatus 10B includes a plurality of flow rate controllers 81a, 81b, and 81c, instead of the flow rate controller 81. Each of the flow rate controllers 81a, 81b, and 81c is sequentially used as a second flow rate controller in the method MT2.

Each of the flow rate controllers 81a, 81b, and 81c is a device that controls the flow rate of gas. The gas output from each of the flow rate controllers 81a, 81b, and 81c is added to the gas output from the first flow rate controller 61 in the downstream of the first flow rate controller 61 and the upstream of the gas ejection unit 30. The flow rate controller 81a is connected to a gas source 84a via a valve 62 on the primary side of the flow rate controller 81a. The flow rate controller 81a is connected to the first pipe 78a via a valve 83a on the secondary side of the flow rate controller 81a, and a second pipe 85a. The flow rate controller 81b is connected to a gas source 84b via a valve 82b on the primary side of the flow rate controller 81b. The flow rate controller 81b is connected to the first pipe 78b via a valve 83b on the secondary side of the flow rate controller 81b, and a second pipe 85b. The flow rate controller 81c is connected to a gas source 84c via a valve 82c on the primary side of the flow rate controller 81c. The flow rate controller 81c is connected to the first pipe 78c via a valve 83c on the secondary side of the flow rate controller 81c, and a second pipe 85c.

In one exemplary embodiment, the flow path length from each of the flow rate controllers 81a, 81b, and 81c to the opening end of the shower plate 34 on the chamber 12c side is equal to or less than 1.5 m. Specifically, in the plasma processing apparatus 10B, the shortest flow path length from the output end of the flow rate controller 81a to the opening ends of the plurality of gas ejection holes 35 of the gas ejection hole group Ga on the chamber 12c side through the second pipe 85a, the first pipe 78a, and the gas diffusion chamber 37a is equal to or less than 1.5 m. Further, the shortest flow path length from the output end of the flow rate controller 81b to the opening ends of the plurality of gas ejection holes 35 of the gas ejection hole group Gb on the chamber 12c side through the second pipe 85b, the first pipe 78b, and the gas diffusion chamber 37b is equal to or less than 1.5 m. Further, the shortest flow path length from the output end of the flow rate controller 81c to the opening ends of the plurality of gas ejection holes 35 of the gas ejection hole group Gc on the chamber 12c side through the second pipe 85c, the first pipe 78c, and the gas diffusion chamber 37c is equal to or less than 1.5 m.

Each of the flow rate controllers 81a, 81b, and 81c is a pressure control type flow rate controller. As each of the flow rate controllers 81a, 81b, and 81c, the flow rate controller FC1 illustrated in FIG. 3 or the flow rate controller FC2 illustrated in FIG. 4 is used.

Meanwhile, a controller Cnt of the plasma processing apparatus 10B may control the respective units of the plasma processing apparatus 10B in the method MT2, and further, execute calculations to be described later in the method MT2.

Hereinafter, the method MT2 will be described in detail by describing a case where the method MT2 is applied to the plasma processing apparatus 10B, as an example. Meanwhile, in the method MT2, the pressure gauge of each of the flow rate controllers 81a, 81b, and 81c is used for the pressure measurement. As each of the flow rate controllers 81a, 81b, and 81c, either the flow rate controller FC1 or the flow rate controller FC2 is used. When the flow rate controller FC1 is used as each of the flow rate controllers 81a, 81b, and 81c, the pressure gauge used for the pressure measurement in the method MT2 may be any one of the pressure gauges Pa and Pb. Further, when the flow rate controller FC2 is used as each of the flow rate controllers 81a, 81b, and 81c, the pressure gauge used for the pressure measurement in the method MT2 is the pressure gauge Pa. In the following descriptions, the pressure gauge of each of the flow rate controllers 81a, 81b, and 81c which is used for the pressure measurement in the method MT2 will be referred to as a "pressure gauge P."

In the method MT2, a sequence SQ1 including steps ST11 to ST15 is executed a plurality of times. When the sequence SQ1 is executed a plurality of times, the plurality of gas ejection hole groups Ga, Gb, and Gc are sequentially selected. In the example described below, it is assumed that the gas ejection hole group Ga is selected as an inspection target in a first sequence SQ1, the gas ejection hole group Gb is selected as an inspection target in a second sequence SQ1, and the gas ejection hole group Gc is selected as an inspection target in a third sequence SQ1. Meanwhile, the order of selecting the plurality of gas ejection hole groups Ga, Gb, and Gc may be arbitrary.

In each sequence SQ1, the step ST11 is executed. In the step ST11, setting of the various valves is performed. Specifically, the valve 62 on the primary side of the first flow rate controller 61 and the valve 63 on the secondary side thereof are opened. Further, among the gas lines 74a, 74b, and 74c of the flow splitter 70, two valves of a gas line that supplies gas to a selected gas ejection hole group are opened, and two valves of each of the other gas lines are closed. For example, in the step ST11 of the first sequence SQ1, the two valves 76a and 77a of the gas line 74a are opened, and the valves 76b and 77b and the valves 76c and 77c are closed. In the step ST11 of the second sequence SQ1, the two valves 76b and 77b of the gas line 74b are opened, and the valves 76a and 77a and the valves 76c and 77c are closed. In the step ST11 of the third sequence SQ1, the two valves 76c and 77c of the gas line 74c are opened, and the valves 76a and 77a and the valves 76b and 77b are closed.

Further, in the step ST11, the valve on the primary side of one flow rate controller (hereinafter, referred to as a "flow rate controller 81S") among the flow rate controllers 81a, 81b, and 81c which is connected to one first pipe (hereinafter, referred to as a "first pipe 78S") among the plurality of first pipes 78a, 78b, and 78c which is connected to a selected gas ejection hole group is closed, and the valve of the secondary side of the flow rate controller 81S is opened. Further, among the flow rate controllers 81a, 81b, and 81c, the valves on the primary and secondary sides of each of the flow rate controllers other than the flow rate controller 81S are closed. For example, in the step ST11 of the first sequence SQ1, the valve 83a on the secondary side of the flow rate controller 81a is opened, and the valves 82a, 82b, 83b, 82c, and 83c are closed. In the step ST11 of the second sequence SQ1, the valve 83b on the secondary side of the flow rate controller 81b is opened, and the valves 82a, 83a, 82b, 82c, and 83c are closed. In the step ST11 of the third sequence SQ1, the valve 83c on the secondary side of the flow rate controller 81c is opened, and the valves 82a, 83a, 82b, 83b, and 82c are closed.

In a subsequent step ST12, the flow rate of the gas output from the first flow rate controller 61 is set to a designated flow rate. By executing the step ST 12, the gas output from the first flow rate controller 61 is supplied to the gas ejection unit 30 through the first pipe 78S, and also supplied to the flow path FP inside the flow rate controller 81S connected to the first pipe 78S.

In a subsequent step ST13, it is determined whether a value of the pressure measured by the pressure gauge P of the flow rate controller 81S becomes stable. In an example, it is determined whether a fluctuation amount of the value of the pressure measured by the pressure gauge P of the flow rate controller 81S is equal to or less than a predetermined value. For example, in the step ST13 of the first sequence SQ1, it is determined whether a value of the pressure measured by the pressure gauge P of the flow rate controller 81a becomes stable. In the step ST13 of the second sequence SQ1, it is determined whether a value of the pressure measured by the pressure gauge P of the flow rate controller 81b becomes stable. In the step ST13 of the third sequence SQ1, it is determined whether a value of the pressure measured by the pressure gauge P of the flow rate controller 81c becomes stable.

When it is determined in the step ST13 that the value of the pressure does not become stable, the step ST13 is executed again after elapse of predetermined time. Meanwhile, when it is determined in the step ST13 that the value of the pressure becomes stable, a step ST14 is executed.

In the step ST14, in a state where the gas output from the first flow rate controller 61 is supplied to the gas ejection unit 30 and the flow path FP inside the flow rate controller 81S, a measurement value indicating the pressure in the flow path FP inside the flow rate controller 81S is acquired using the pressure gauge P of the flow rate controller 81S. In one exemplary embodiment, the measurement value acquired in the step ST14 may be an average value of a plurality of instantaneous values of the pressure in the flow path FP of the flow controller 81S. The plurality of instantaneous values are acquired for time length of, for example, 10 seconds.

In a subsequent step ST15, it is determined whether the inspection using all the plurality of different flow rates has been completed. Specifically, it is determined whether all the plurality of different flow rates have been designated in the first flow rate controller 61. When it is determined in the step ST15 that the inspection using all the flow rates has not been completed, the processing from the step ST12 is executed again. When the step ST12 is executed again, the flow rate of the gas output from the first flow rate controller 61 is set to another flow rate among the plurality of different flow rates that has not been used for the inspection. When the sequence SQ2 including the steps ST12 and ST14 is repeated, a plurality of measurement values may be obtained.

Meanwhile, when it is determined in the step ST15 that the inspection using all the flow rates has been completed, a step ST16 is executed. In the step ST16, it is determined that the selection of all the gas ejection hole groups has been completed. When it is determined that the selection of all the gas ejection hole groups has not been completed, a gas ejection hole group that has not yet been selected is selected, and each of the steps of the sequence SQ1 is executed again. Meanwhile, when it is determined in the step ST16 that the selection of all the gas ejection hole groups has been completed, the process proceeds to a step ST17. In this way, in the method MT2, a plurality of measurement values may be obtained for each of the plurality of gas ejection hole groups Ga, Gb, and Gc prior to executing the step ST17. That is, a plurality of sets of measurement values may be obtained.

In the step ST17, the plurality of sets of measurement values are compared with a plurality of sets of reference values that are prepared in advance, respectively. That is, the plurality of measurement values acquired for each of the plurality of gas ejection hole groups Ga, Gb, and Gc are compared with a plurality of corresponding reference values that are prepared in advance for each of the plurality of gas ejection hole groups Ga, Gb, and Gc. For example, when at least one of the plurality of sets of measurement values is largely different from its corresponding reference value, abnormality of the shower plate 34 is detected. More specifically, when an absolute value of a difference between at least one of the plurality of sets of measurement values and its corresponding reference value is larger than a threshold value, abnormality of the shower plate 34 is detected. Alternatively, when the sum of absolute values of differences between the plurality of sets of measurement values and the plurality of sets of reference values, respectively, is larger than a threshold value, abnormality of the shower plate 34 is detected.

In a first example, the plurality of sets of reference values are a plurality of sets of measurement values acquired by executing the method MT2 when the shower plate 34 is initially introduced in the plasma processing apparatus 10B. In a second example, the plurality of sets of reference values are a plurality of sets of measurement values acquired by applying the method MT2 to another plasma processing apparatus that has the same configuration as that of the plasma processing apparatus 10B and executes the same processing in parallel with the plasma processing apparatus 10B. In a third example, the plurality of sets of reference values are a plurality of sets of measurement values acquired by applying the method MT2 to a reference plasma processing apparatus that has the same configuration as that of the plasma processing apparatus 10B. Meanwhile, the reference plasma processing apparatus may have a shower plate on which a plurality of gas ejection holes each having a substantially similar diameter to the designed value are formed.

According to the method MT2, the shower plate 34 may be inspected as in the method MT1. Further, in the method MT2, a pressure measurement value reflecting the diameters of the gas ejection holes of each of the plurality of gas ejection hole groups is acquired. Thus, several measurement values reflecting distribution of the diameters of the gas ejection holes in the radial direction of the shower plate 34 may be obtained.

Further, as described above, in one exemplary embodiment, the measurement value is an average value of a plurality of instantaneous values of the pressure measured by the pressure gauge P. Thus, in this exemplary embodiment, the error caused by the measurement accuracy of the pressure gauge P is suppressed.

Further, as described above, in one exemplary embodiment, the flow path length from each of the flow rate controllers 81a, 81b, and 81c to the opening end of the shower plate 34 on the chamber 12c side is equal to or less than 1.5 m. In this exemplary embodiment, the pressure measured by the pressure gauge P largely varies depending on a change of the diameters of the gas ejection holes 35. Therefore, the change of the diameters of the gas ejection holes 35 may be detected with high sensitivity.

Further, the above-described reference values in the first example are measurement values acquired by executing the method MT2 when the shower plate 34 is initially introduced in the plasma processing apparatus 10B. Thus, by comparing the reference values of the first example and the measurement values with each other, the occurrence of deterioration of the shower plate 34 is detected.

In addition, the above-described reference values in the second example are measurement values acquired by applying the method MT2 to another plasma processing apparatus that has the same configuration as that of the plasma processing apparatus 10B and executes the same processing in parallel with the plasma processing apparatus 10B. Thus, by comparing the reference values of the second example and the measurement values with each other, the occurrence of a machine difference related to the shower plate among the plurality of plasma processing apparatuses is detected.

In addition, the above-described reference values in the third example are measurement values acquired by applying the method MT2 to a reference plasma processing apparatus that has the same configuration as that of the plasma processing apparatus 10B. The reference plasma processing apparatus may have a shower plate on which a plurality of gas ejection holes each having a substantially similar diameter to the designed value are formed. Thus, by comparing the reference values of the third example and the measurement values with each other, the occurrence of a difference between the diameters of the gas ejection holes 35 of the shower plate 34 of the plasma processing apparatus 10B and the designed value.

The various exemplary embodiments have been described. However, the present disclosure is not limited to the foregoing exemplary embodiments and may be configured in various modified aspects. For example, the flow splitter 70 may be omitted from the plasma processing apparatus 10. In this case, the plurality of gas ejection holes 35 of the shower plate 34 may be connected to a single gas diffusion chamber, and the second pipe 85 may be connected to a pipe connecting the valve 63 and the single gas diffusion chamber to each other. Alternatively, gas output from a plurality of first flow rate controllers similar to the first flow rate controller 61 may be supplied to a plurality of gas diffusion chambers, respectively, and the second pipe 85 may be connected to one of a plurality of pipes connecting the plurality of first flow rate controllers and the plurality of gas diffusion chambers to each other, respectively.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for inspecting a shower plate of a plasma processing apparatus comprising:
    a chamber body;
    a placing table that is provided inside a chamber provided by the chamber body; and
    a gas ejection unit that is provided above the placing table and has the shower plate including a plurality of gas ejection holes formed therein,
    the method comprising:
    setting a flow rate of gas output from a first flow rate controller; and
    acquiring a measurement value indicating a pressure in a flow path inside a second pressure control type flow rate controller by using a pressure gauge of the second flow rate controller in a state where the gas output from the first flow rate controller at the set flow rate is supplied to the gas ejection unit and branched between the first flow rate controller and the gas ejection unit so as to be supplied to the flow path inside the second flow rate controller.

2. The method of claim 1, wherein the measurement value is an average value of a plurality of instantaneous values of the pressure.

3. The method of claim 1, wherein a flow path length from the second flow rate controller to an opening end of the shower plate on a side of the chamber is equal to or less than 1.5 m.

4. The method of claim 1, wherein the plurality of gas ejection holes constitute a plurality of gas ejection hole groups,
    the plasma processing apparatus further comprises a flow splitter having an input connected to the first flow rate controller and a plurality of outputs connected to the plurality of gas ejection hole groups, respectively, and
    a pipe extending from the second flow rate controller is connected to a pipe connecting one of the plurality of outputs and one gas ejection hole group of the plurality of gas ejection hole groups to each other.

5. The method of claim 1, wherein the plurality of gas ejection holes constitute a plurality of gas ejection hole groups,
    the plasma processing apparatus further comprises a flow splitter having an input connected to the first flow rate controller and a plurality of outputs connected to the plurality of gas ejection hole groups, respectively, and
    a pipe extending from the second flow rate controller is connected to a pipe connecting the input of the flow splitter and the first flow rate controller to each other.

6. The method of claim 1, wherein the plurality of gas ejection holes constitute a plurality of gas ejection hole groups,
    the plurality of gas ejection hole groups are formed on a plurality of areas of the shower plate that are coaxial with an axis of the shower plate extending in a plate thickness direction, respectively,
    the plasma processing apparatus further comprises:
    a flow splitter having an input connected to the first flow rate controller and a plurality of outputs connected to the plurality of gas ejection hole groups, respectively;
    a plurality of first pipes that connect the plurality of outputs of the flow splitter and the plurality of gas ejection hole groups to each other, respectively;
    a plurality of pressure control type flow rate controllers; and
    a plurality of second pipes that connect the plurality of flow rate controllers and the plurality of first pipes to each other, respectively,
    in the acquiring the measurement value, a measurement value indicating a pressure in a flow path inside one flow rate controller of the plurality of flow rate controllers that is connected to the one first pipe, as the second flow rate controller, is acquired using a pressure gauge of the one flow rate controller in a state where the gas output from the first flow rate controller at the set flow rate is supplied to the gas ejection unit through one first pipe of the plurality of first pipes that is connected to one gas ejection hole group selected from the plurality of gas ejection hole groups, and supplied to the flow path inside the one flow rate controller, and the acquiring the measurement value is executed in a manner that each of the plurality of gas ejection hole groups is sequentially selected as the one gas ejection hole group.

7. The method of claim 1, further comprising:
comparing the measurement value with a reference value that is prepared in advance.

8. The method of claim 1, wherein a sequence including the setting the flow rate and the acquiring the measurement value is repeated using different flow rates, each as the flow rate, and a plurality of measurement values including the measurement value are acquired.

\* \* \* \* \*